United States Patent [19]

Meier et al.

[11] Patent Number: 5,292,966
[45] Date of Patent: Mar. 8, 1994

[54] PROCESS FOR THE PREPARATION OF 2-NITRO-3, 6-DICHLOROPHENOL

[75] Inventors: Michael Meier, Frankfurt am Main; Heinz-Georg Kautz, Birstein, both of Fed. Rep. of Germany

[73] Assignee: Hoechst Aktiengesellschaft, Frankfurt, Fed. Rep. of Germany

[21] Appl. No.: 33,110

[22] Filed: Mar. 16, 1993

[30] Foreign Application Priority Data

Mar. 18, 1992 [DE] Fed. Rep. of Germany ....... 4208630

[51] Int. Cl.$^5$ .................. C07C 205/26; C07C 205/20
[52] U.S. Cl. ................................. 568/709; 568/713
[58] Field of Search .................. 568/713, 709

[56] References Cited

U.S. PATENT DOCUMENTS

| 3,903,178 | 9/1975 | Nakamura et al. | 568/709 |
| 4,038,328 | 7/1977 | Pelster et al. | 568/709 |
| 5,012,015 | 4/1991 | Terao et al. | 568/709 |
| 5,136,109 | 8/1992 | Kimura et al. | 568/709 |

FOREIGN PATENT DOCUMENTS

| 0473464 | 3/1992 | European Pat. Off. | |
| 2501899 | 7/1976 | Fed. Rep. of Germany | 568/709 |
| 1228943 | 9/1989 | Japan | 568/709 |
| 1258649 | 10/1989 | Japan | 568/709 |

OTHER PUBLICATIONS

Journal of the Chemical Society, Herbert Henry Hodgson and Arnold Kershaw, Dec. 1929, pp. 2917–2923.
Journal of Heterocyclic Chemistry, H. M. Grotta, T. F. Page, Jr., C. J. Riggle, and A. A. Manian, Dec. 1967, vol. 4, pp. 611–618.

Primary Examiner—Werren B. Lone
Attorney, Agent, or Firm—Connolly and Hutz

[57] ABSTRACT

2-Nitro-3,6-dichlorophenol is prepared by sulfonation of 2,5-dichlorophenol and subsequent nitration and desulfonation, in which the nitration is carried out by metering in a nitrating acid composed of 98 to 100% strength nitric acid and 96 to 100% strength sulfuric acid at temperatures from −15° to 35° C. and a metering time of at least 1 hour.

20 Claims, No Drawings

PROCESS FOR THE PREPARATION OF 2-NITRO-3, 6-DICHLOROPHENOL

The present invention relates to an improved process for the preparation of 2-nitro-3,6-dichlorophenol by sulfonation of 2,5-dichlorophenol followed by nitration and desulfonation.

2-Nitro-3,6-dichlorophenol is a valuable intermediate for the preparation of pharmaceuticals.

It was described in J. Chem. Soc. 1929, 2917-2923 (H. H. Hodgson, A. Kershaw) that 2,5-dichlorophenol can be sulfonated with oleum, this can subsequently be nitrated with a mixture of nitric acid and oleum and the sulfonyl group can then be removed again. However, the information on the reaction parameters is so incomplete that this process is not reproducible. Also, the ratio in which the nitric acid is employed is highly substoichiometric.

It was already recognized by H. M. Grotta, T. F. Page Jr., J. Riggle, A. A. Manian, J. Heterocycl. Chem. 4, 611-618 (1967) that it is impossible to carry out the above-mentioned process in the form in which it is described. The authors modified this process in such a way that they prepared 2-nitro-3,6-dichlorophenol by sulfonation with oleum at 80°-90° C. followed by nitration by adding a mixture of nitric acid and oleum over 30 minutes at 0° C. and after-reaction for 17 hours at 25° C. and a further 5 hours at 60° C. After subsequent desulfonation, they obtained the product in a yield of 51%. The disadvantage of this process was, and is, the use of oleum even in the nitration step, the unduly long reaction times and the low yields.

It is also known to react p-dichlorobenzene photochemically with NO (K. Nojima, K. Sauro, Chemosphere 9, 437-440 (1980)) and to react phenol with nitryl chloride in methylene chloride at −50° C. (M. J. Collis, D. R. Goddard, J. Chem. Soc. 1958, 1952-1955). However, both reactions cannot be utilized industrially since the 2-nitro-3,6-dichlorophenol is formed in low yield and in the form of a mixture with other isomers.

There was therefore a demand for an economical process for the preparation of isomer-free 2-nitro-3,6-dichlorophenol in good yields which can be carried out readily on an industrial scale and which preferably dispenses with the use of oleum.

It has now been found that isomer-free 2-nitro-3,6-dichlorophenol can be prepared in high yields by nitrating sulfonated 2,5-dichlorophenol by metering in a nitrating acid composed of nitric acid and sulfuric acid over a period of at least 1 hour, the temperature being kept below 35° C. during the nitration time, and subsequently desulfonating the product.

The invention therefore relates to a process for the preparation of 2-nitro-3,6-dichlorophenol by sulfonation of 2,5-dichlorophenol and subsequent nitration and desulfonation, which comprises carrying out the nitration by metering in a nitrating acid composed of 98 to 100% strength, preferably 100% strength, nitric acid and 96 to 100% strength, preferably 100% strength, sulfuric acid at temperatures from −15° to 35° C. and a metering time of at least 1 hour.

In general, the sulfuric acid is employed in an amount of 1.5 to 10 times, preferably 2 to 8 times, particularly preferably 4 to 6 times, the amount of weight relative to the nitric acid. The nitric acid itself is expediently employed in an amount of 0.8 to 1.3 mol, preferably in an amount of 0.9 to 1.2 mol and particularly preferably in an amount of 1.0 to 1.1 mol, per mol of 2,5-dichlorophenol.

In the process according to the invention, the nitration is carried out at temperatures from −15° to 35° C. Higher temperatures result increasingly in undesired dinitration reactions. Too rapid metering in of the nitrating acid also results in an increase in dinitration reactions. The nitration is preferably carried out at temperatures from 0° to 25° C., expediently at 5° to 20° C. The time during which the nitrating acid is added is advantageously at least 1.5 hours, but preferably at least 2 hours. However, times which greatly exceed approx. 10 hours are pointless in practice.

The sulfonation and desulfonation can be carried out in a manner known per se. For example, sulfonation may be carried out using oleum. However, it is preferred to carry out the sulfonation using 98 to 100% strength, advantageously 100% strength, sulfuric acid at temperatures from 70° to 130° C. The sulfuric acid or the oleum is preferably employed in approximately 2.5 to 12 times, preferably 4 to 8 times, the amount of weight relative to 2,5-dichlorophenol.

In general, a procedure is followed in which 2,5-dichlorophenol is treated with 100% strength sulfuric acid, and stirring of the reaction mixture is continued for approx. 1 hour at 70° to 130° C. Alternatively, the sulfuric acid can be introduced first and the 2,5-dichlorophenol is then metered in. Once nitration has taken place, the product is desulfonated, for example by treating the reaction mixture with water, subjecting it, if appropriate, to steam distillation at temperatures from approx. 150° to 170° C., and isolating the 2-nitro-3,6-dichlorophenol which distills over. Alternatively, it is possible to treat the reaction mixture with water when the nitration has ended, to heat the mixture for approx. 4 hours at approx. 150° to 170° C., to cool it with stirring, and to isolate the product which has precipitated without steam distillation.

It is surprising that the process according to the invention allows the nitrating times to be reduced markedly from above 20 hours to below 5 hours despite the use of less reactive nitrating acid than in the prior art, allowing the yields and purities of the 2-nitro-3,6-dichlorophenol formed to be improved drastically. Equally, the advantage that the process according to the invention permits the sulfonation to be carried out with sulfuric acid instead of oleum could not have been expected.

EXAMPLES 1. 81.5 g (0.5 mol) of 2,5-dichlorophenol were introduced into a 1 l four-necked flask equipped with stirrer, internal thermometer and dropping funnel, 222 g of 100% strength sulfuric acid were added, and the mixture was subsequently stirred for 1 hour at 100° C. The reaction mixture was cooled to 15° C., and a mixture of 33.1 g (0.525 mol) of 100% strength nitric acid and 165.5 g of 100% strength sulfuric acid was metered in at 15° C. in the course of 2 hours. Stirring of the mixture was subsequently continued for 30 minutes at 15° C., and the reaction mixture was treated with 100 ml of water and subjected to steam distillation at 150° to 170° C. A total of 980 g distils over. The 2-nitro-3,6-dichlorophenol, which had precipitated in the distillate, was filtered off. 99.3 g of moist product with a water content of 8.8% and a purity of 98.2% (according to GC, silylation using BSTFA) were obtained. This corresponds to a yield of 85.5% (calculated as 100% pure). The melting point was 48° C.

$^1$H-NMR (CDCl$_3$): δ=7.05 (d, $^3J_{H,H}$=10 Hz; 1 H; ArH), 7.45 (d, $^3J_{H,H}$=10 Hz); 1 H; ArH), 7.9 (broad; 1 H; OH).

2. 500 g of 100% strength sulfuric acid were added to 122.25 g (0.75 mol) of 2,5-dichlorophenol, and the mixture was subsequently stirred for 1 hour at 100° C. The batch was subsequently cooled to 0° C., and a mixture of 49.6 g (0.79 mol) of 100% strength nitric acid and 246.5 g of 100% strength sulfuric acid was metered in at 0° C. in the course of 2 hours. The reaction mixture was subsequently treated with 100 ml of water and subjected to steam distillation at 150° to 170° C. A total of 1854 g distils over. The 2-nitro-3,6-dichlorophenol, which had precipitated in the distillate, was filtered off. 152.4 g of moist product with a water content of 10.5% and a purity of 97.5% (according to GC) were obtained. This corresponds to a yield of 86.1% (calculated as 100% pure). The melting point was 46° C., and the spectroscopic data were identical to those of Example 1.

3. 555 g of 100% strength sulfuric acid were added to 122.25 g (0.75 mol) of 2,5-dichlorophenol, and the mixture was subsequently stirred for 1 hour at 120° C. The batch was subsequently cooled to 0° C., and a mixture of 49.6 g (0.79 mol) of 100% strength nitric acid and 246.5 g of 100% strength sulfuric acid was metered in at 0° C. in the course of 2 hours. The reaction mixture was subsequently treated with 100 ml of water and subjected to steam distillation at 150° to 170° C. A total of 1263 g distils over. The 2-nitro-3,6-dichlorophenol, which had precipitated in the distillate, was filtered off. 151.1 g of moist product with a water content of 9.2% and a purity of 96.0% (according to GC) were obtained. This corresponds to a yield of 85.3% (calculated as 100% pure). The melting point was 47° C., and the spectroscopic data were identical to those of Example 1.

4. 500 g of 100% strength sulfuric acid were added to 122.25 g (0.75 mol) of 2,5-dichlorophenol, and the mixture was subsequently stirred for 1 hour at 100° C. The batch was subsequently cooled to 15° C., and a mixture of 49.6 g (0.79 mol) of 100% strength nitric acid and 246.5 g of 100% strength sulfuric acid was metered in at 15° C. in the course of 2 hours. The reaction mixture was subsequently treated with 250 ml of water and heated for 4 hours at 150°-160° C. When cold, the reaction mixture was poured onto ice, and the product which had precipitated was filtered off with suction. 2-Nitro-3,6-dichlorophenol was resuspended in 250 ml of water and again subjected to filtration with suction. 150.0 g of moist product with a water content of 2.5% and a purity of 93.8% (according to GC) were obtained. This corresponds to a yield of 87.9% (calculated as 100% pure). The melting point was 42° C. and the spectroscopic data were identical to those of Example 1.

5. 640 g of 100% strength sulfuric acid were added to 122.25 g (0.75 mol) of 2,5-dichlorophenol, and the mixture was subsequently stirred for 1 hour at 100° C. The batch was subsequently cooled to 15° C., and a mixture of 48.3 g (0.766 mol) of 100% strength nitric acid and 96.6 g of 100% strength sulfuric acid was metered in at 10°-15° C. in the course of 4 hours. The reaction mixture was subsequently treated with 100 ml of water and subjected to steam distillation at 150° to 170° C. A total of 1228 g distils over. The 2-nitro-3,6-dichlorophenol, which had precipitated in the distillate, was filtered off. 148.6 g of moist product with a water content of 4.6% and a purity of 95.4% (according to GC) were obtained. This corresponds to a yield of 86.6% (calculated as 100% pure). The melting point was 46° C., and the spectroscopic data were identical to those of Example 1.

We claim:

1. A process for the preparation of 2-nitro-3,6-dichlorophenol by sulfonation of 2,5-dichlorophenol and subsequent nitration and desulfonation, which comprises carrying out the nitration by metering in a nitrating acid comprising 98 to 100% strength nitric acid and 96 to 100% strength sulfuric acid at temperatures from −15° to 35° C. and for a metering time of at least 1 hour.

2. The process as claimed in claim 1, wherein the strength of the nitric acid and the sulfuric acid is 100%.

3. The process as claimed in claim 1, wherein the amount of sulfuric acid employed is 1.5 to 10 times the amount of weight relative to the nitric acid.

4. The process as claimed in claim 1, wherein the nitric acid is employed in an amount of 0.8 to 1.3 mol, per mole of 2,5-dichlorophenol.

5. The process as claimed in claim 1, wherein the nitration is carried out at temperatures from 0° to 25° C.

6. The process as claimed in claim 1, wherein the metering time is at least 1.5 hours.

7. The process as claimed in claim 1, wherein the sulfonation is carried out using 98 to 100% strength sulfuric acid.

8. The process as claimed in claim 7, wherein the amount of sulfuric acid employed is 2.5 to 12 times the amount of weight relative to 2,5-dichlorophenol.

9. The process as claimed in claim 1, wherein the sulfonation is carried out at 70° to 130° C.

10. The process as claimed in claim 1, wherein the reaction mixture obtained in the nitration step is treated with water and subjected to steam distillation at temperatures from 150° to 170° C., and the 2-nitro-3,6-dichlorophenol, which is obtained in the distillate, is filtered off.

11. The process as claimed in claim 1, wherein the reaction mixture obtained in the nitration step is treated with water and heated at temperatures from 150° to 170° C., and the 2-nitro-3,6-dichlorophenol which has precipitated is filtered off.

12. The process as claimed in claim 1, wherein the amount of sulfuric acid employed is 2 to 8 times the amount relative to the nitric acid.

13. The process as claimed in claim 1, wherein the nitric acid is employed in an amount of 0.9 to 1.2 mol per mole of 2,5-dichlorophenol.

14. The process as claimed in claim 1, wherein the nitration is carried out at temperatures from 5° to 20° C.

15. The process as claimed in claim 1, wherein the metering time is at least 2 hours.

16. The process as claimed in claim 1, wherein the sulfonation is carried out using 100% strength sulfuric acid.

17. The process as claimed in claim 16, wherein the amount of sulfuric acid employed his 4 to 8 times the amount of weight relative to 2,5-dichlorophenol.

18. The process as claimed in claim 1, wherein:
the amount of sulfuric acid employed is 4 to 6 times the amount of weight relative to the nitric acid or 4 to 8 times the amount of weight relative to 2,5-dichlorophenol; and
the nitric acid is employed in an amount of 1.0 to 1.1 mole per mole of 2,5-dichlorophenol.

19. A process for the preparation of 2-nitro-3,6-dichlorophenol from 2,5-dichlorophenol, comprising:

a. sulfonating the 2,5-dichlorophenol,
b. nitrating the resulting sulfonated product by metering in a nitrating acid comprising 98 to 100% strength nitric acid and 96 to 100% strength sulfuric acid at a temperature in the range of −15° to 35° C. and for a metering time of at least one hour, and
c. desulfonating the resulting nitrated product, and recovering 2-nitro-3,6-dichlorophenol.

20. A process for the preparation of 2-nitro-3,6-dichlorophenol by sulfonation of 2,5-dichlorophenol and subsequent nitration and desulfonation, which comprises carrying out the nitration by metering in a nitrating acid compose of 90 to 100% strength nitric acid and 96 to 100% strength sulfuric acid at temperature from −15° to 35° C. and metering time of at least 1 hour, and wherein said desulfonation is carried out using 98 to 100% strength sulfuric acid, with said amount of sulfuric acid employed being from 2.5 to 12 times the amount of weight relative to 2,5-dichlorophenol and said sulfonation is carried out at 70° to 130° C.

* * * * *